United States Patent [19]
Johnson et al.

[11] Patent Number: 4,939,924
[45] Date of Patent: Jul. 10, 1990

[54] PULSED COULOMETRIC DETECTION WITH AUTOMATIC REJECTION OF BACKGROUND SIGNAL IN SURFACE-OXIDE CATALYZED ANODIC DETECTIONS AT GOLD ELECTRODES IN FLOW-THROUGH CELLS

[75] Inventors: Dennis C. Johnson, Ames, Iowa; Glen G. Neuburger, Freehold, N.J.

[73] Assignee: Iowa State University Research Foundation, Inc., Ames, Iowa

[21] Appl. No.: 249,014

[22] Filed: Sep. 26, 1988

[51] Int. Cl.$^5$ ............ G01N 27/42; G01N 30/62
[52] U.S. Cl. ............ 73/61.1 C; 204/402
[58] Field of Search ............ 204/402, 1 T; 73/61.1 C

[56] References Cited

U.S. PATENT DOCUMENTS 4,566,949 1/1986 Berger ............ 204/1 T

OTHER PUBLICATIONS

Hughes, S. et al., Anal. Chim. Acta., 132, 11, (1981).
Hughes, S. et al., Anal. Chim. Acta., 149, 1, (1983).
Edwards, P. et al., Amer, Lab., 1983, Apr. 1978.
Rocklin, R. D. et al., J. Liq. Chromatogr., 6(9), 1577, (1983).
Neuburger, G. G. et al., Anal. Chem., 59,150, (1987).
Neuburger, G. G. et al., Anal. Chem., 59,203,(1987).
Polta et al., J. Liq. Chromatogr., 6, 1727, (1983).
Polta et al., J. Chromatogr., 324, 407, (1985).
Polta, J. A. et al., J. Electroanal. Chem., 209, 159 (1986).
Polta, T. Z. et al., J. Electroanal. Chem., 209, 171, (1986).
Thomas, M. B. et al., J. Chromatogr., 357, 318 (1986).
Neuburger, G. G. et al., Anal. Chim. Acta., 192, 205, (1987).
Polta, J. A. et al., Anal. Chem., 57, 563, (1985).
Mead, D. A., M. S. Dissertation, "Comparison of Various Reference Electrodes for Pulsed Amperometric Detection of Carbohydrates Under Gradient Chromatographic Conditions", Iowa State University, Ames, IA, (1988).

*Primary Examiner*—G. L. Kaplan
*Attorney, Agent, or Firm*—Flehr, Hohbach, Test, Albritton & Herbert

[57] ABSTRACT

A variation of Pulsed Coulometric Detection (PCD) is described in which the detection potential is scanned in a cyclic fashion during current integration to achieve automatic and virtual elimination of baseline drift caused by surface roughening and changes in pH. The technique is examined at a Au electrode for flow-injection determination if thiourea which is typical of numerous sulfur compounds whose anodic reactions are catalyzed by formation of surface oxide. The baseline decays quickly to a near-zero equilibrium value following start-up and is unchanged for a pH step of ca. 2 units. The technique is concluded to be compatible with pH-gradient chromatography.

10 Claims, 21 Drawing Sheets

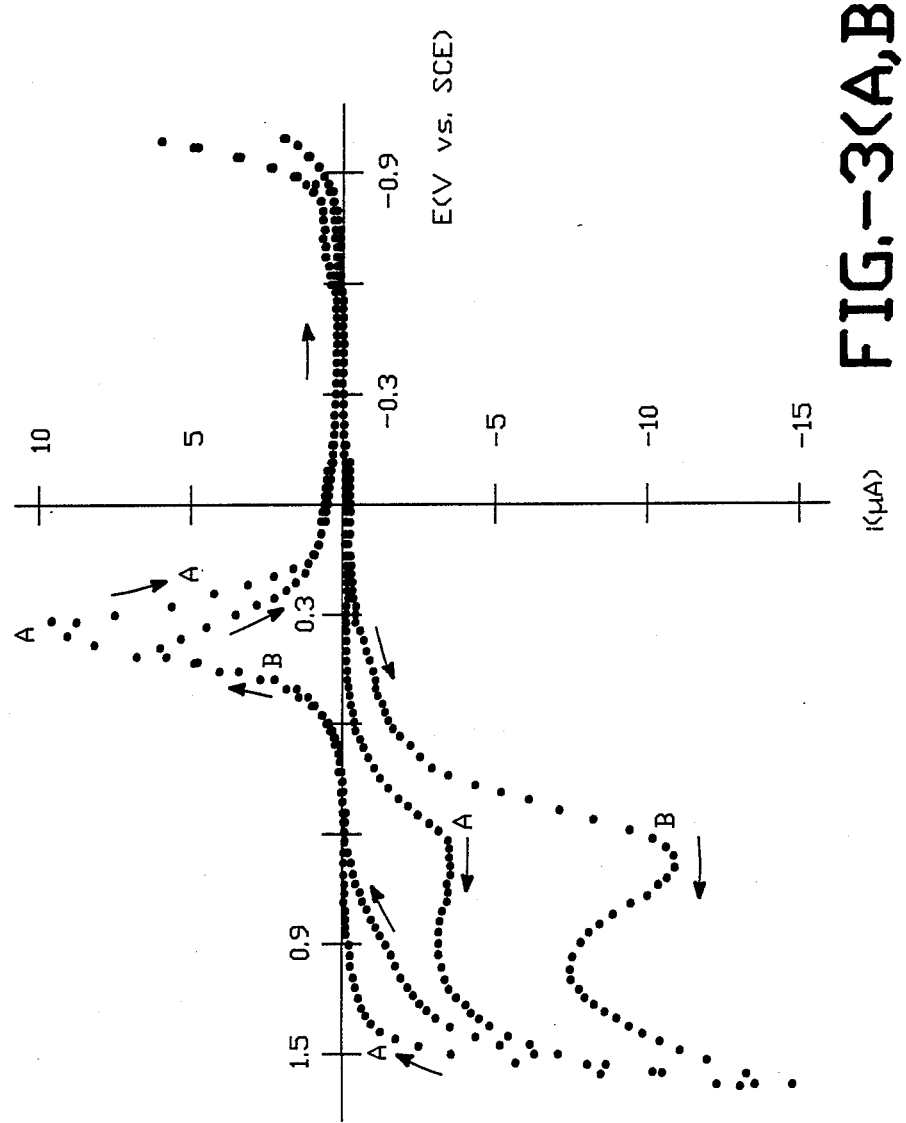

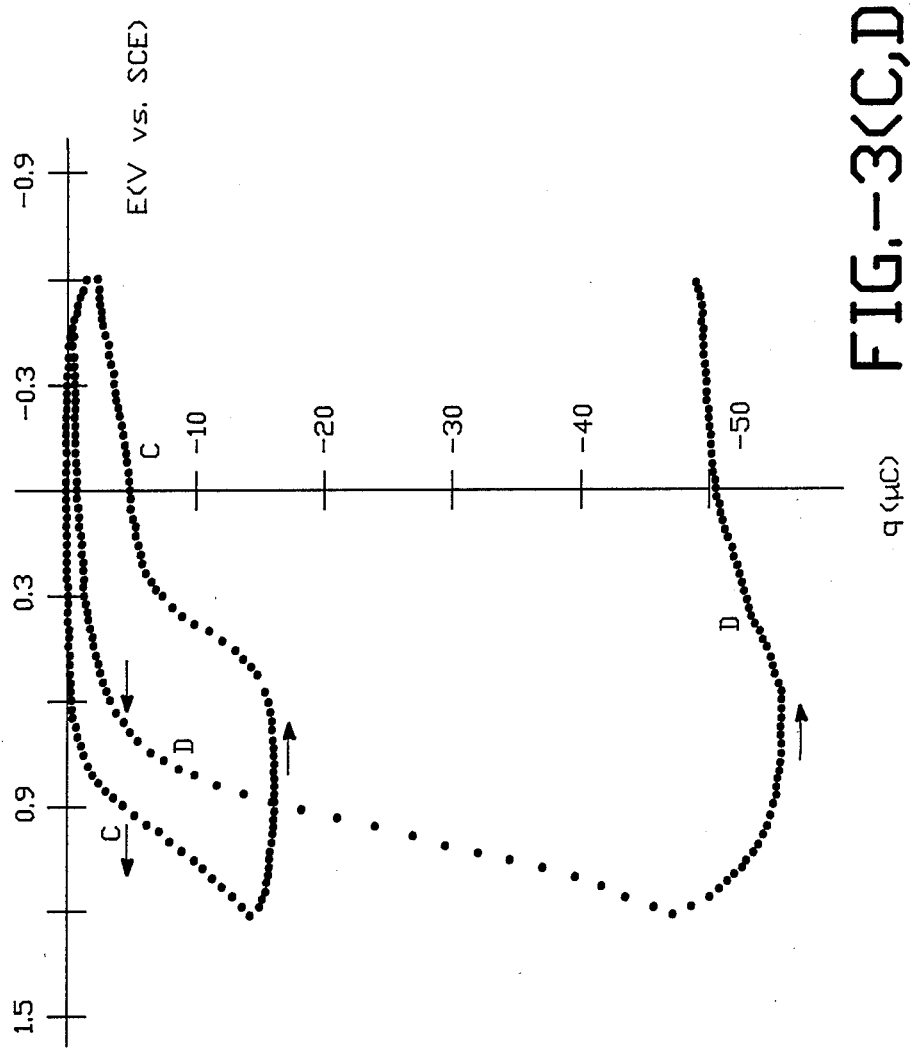

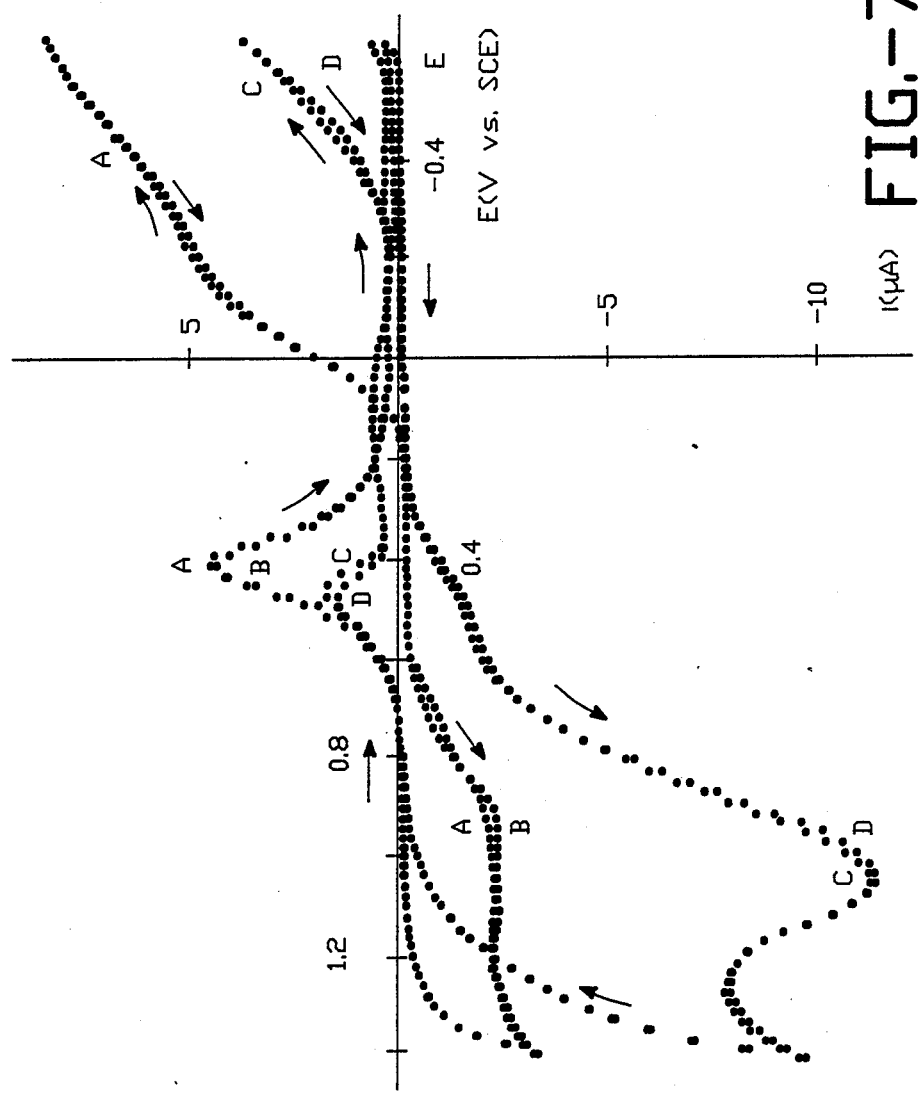

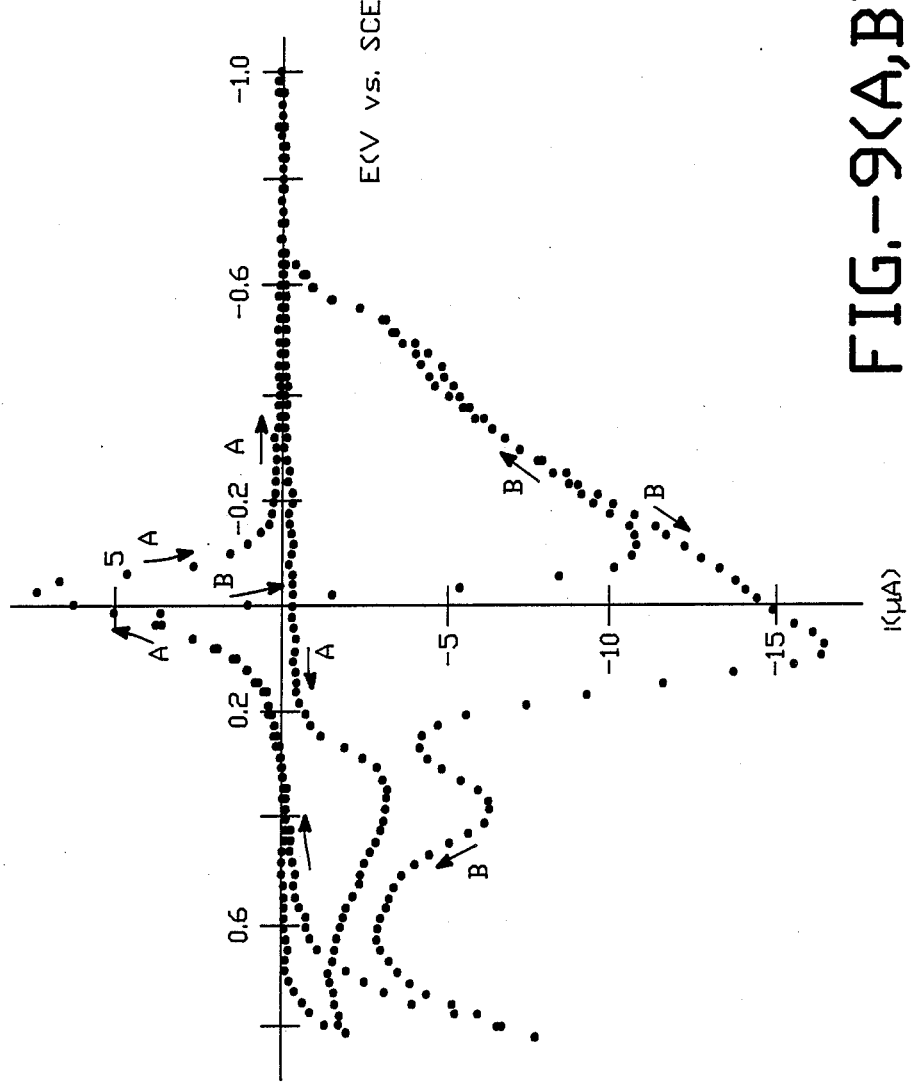

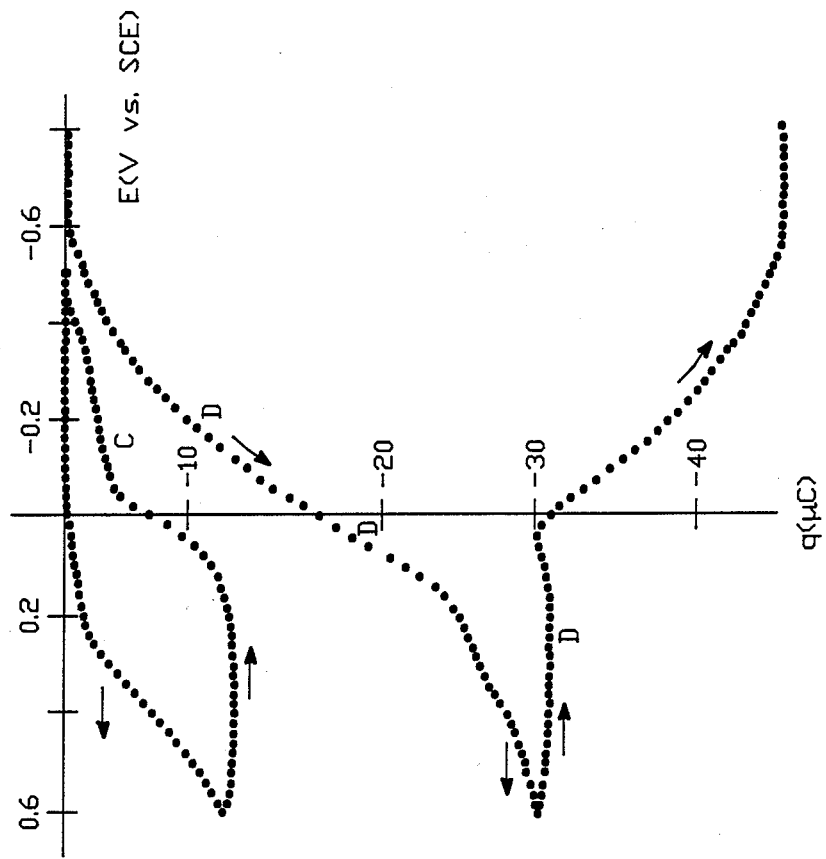

Anion-exchange LC-PAD of the Pierce protein hydrolyzate

Electrode: Au, glass reference
Column: AS-8
Solutions: see Table III
Samples: Pierce protein hydrolyzate,
 $5 \times 10^{-4}$ M each except cystine
 at $2.5 \times 10^{-4}$ M 1) arginine
2) lysine
3) threonine
4) alanine
5) glycine
6) serine
7) valine
8) proline
9) isoleucine
10) leucine
11) methionine
12) histidine
13) phenylalanine
14) glutamic acid
15) aspartic acid
16) cystine
17) tyrosine Waveform:

LC-PCD of the Pierce protein hydrolyzate using a glass reference electrode

Electrode: Au, glass reference
Column: AS-8
Solutions: see Table III
Samples: Pierce protein hydrolyzate, $5 \times 10^{-4}$ M each, except cystine at $2.5 \times 10^{-4}$ M 1) arginine
2) lysine
3) threonine
4) alanine
5) glycine
6) serine
7) valine
8) proline
9) isoleucine
10) leucine
11) methionine
12) histidine
13) phenylalanine
14) glutamic acid
15) aspartic acid
16) cystine
17) tyrosine Waveform:

| | | | | |
|---|---|---|---|---|
| $E_1$: 200 | $E_2$: 800 | $E_3$: 200 | $E_4$: 1000 | $E_5$: -350 |
| $T_a$: 350 | $T_b$: 50 | $T_c$: 5 | $T_d$: 1 | $T_e$: 344 |
| $T_f$: 50 | $T_g$: 10 | $T_h$: 100 | $T_i$: 90 | |

FIG.-12 A

LC-PCD of 20 amino acids

Electrode: Au, glass reference

Column: AS-8

Solutions: see Table III

Samples:
1) arginine
2) lysine
3) glutamine
4) asparagine
5) threonine
6) alanine
7) glycine
8) serine
9) valine
10) proline
11) isoleucine
12) leucine
13) methionine
14) histidine
15) phenylalanine
16) glutamic acid
17) aspartic acid
18) cysteine
19) cystine
20) tyrosine Waveform:

Table III. Solvent system for amino acid separation with the Dionex AS-8 column

---

Solution #1 (regenerant): 0.56 M NaOH/ 0.64 M boric acid

Solution #2: 0.023 M NaOH/ 0.007 M $Na_2B_4O_7$ (0.005 M Na B O substituted for LC-PAD and LC-PCD)

Solution #3: 0.08 M NaOH/ 0.018 M $Na_2B_4O_7$

2% MeOH

Solution #4: 0.4 M NaOAc/ 0.001 M NaOH/ 2% MeOH

Flow rate = 1.0 ml $min^{-1}$

Gradient program

| Time (min) | Sol #1 % | Sol #2 % | Sol #3 % | Sol #4 % | Inj val pos |
|---|---|---|---|---|---|
| 0.0 | – | 100 | – | – | inj |
| 4.0 | – | 100 | – | – | inj |
| 4.1 | 100 | – | – | – | inj |
| 13.9 | 100 | – | – | – | inj |
| 14.0 | – | 100 | – | – | inj |
| 25.8 | – | 100 | – | – | load |
| 26.0 | – | 100 | – | – | inj |
| 36.0 | – | 100 | – | – | inj |
| 40.0 | – | – | 100 | – | inj |
| 46.0 | – | – | 100 | – | inj |
| 46.1 | – | – | 90 | 10 | inj |
| 56.0 | – | – | – | 100 | inj |

FIG.-15

PULSED COULOMETRIC DETECTION WITH AUTOMATIC REJECTION OF BACKGROUND SIGNAL IN SURFACE-OXIDE CATALYZED ANODIC DETECTIONS AT GOLD ELECTRODES IN FLOW-THROUGH CELLS

The United States Government has rights to the invention herein through the National Science Foundation, Contract CHE-8312032, with Iowa State University.

BACKGROUND OF THE INVENTION

Intense interest has developed related to the direct electrochemical detection of aliphatic compounds based on electrocatalytic reactions at noble metal electrodes, chiefly Au and Pt. Electrochemical detection is a widely accepted means of detection in liquid and ion chromatography. Electrochemical detectors operate by applying an electric potential to the working electrode in a flow-through cell. Such detectors typically employ a three-electrode cell including a working electrode, a reference electrode and a counter electrode. The methodology relies on use of multi-step potential waveforms which incorporate a detection operation along with the anodic cleaning and cathodic reactivation of the electrode surface. A typical potential waveform is shown in FIG. 1A. Anodic detection occurs at potential $E_1$ with current sampling during a 16.7-ms period at the end of period $t_1$. The potential then is stepped to $E_2$ (period $t_2$), for oxidative cleaning of the electrode surface, and subsequently to $E_3$ (period $t_3$) for reactivation by cathodic dissolution of the surface oxide formed at $E_1$ and/or $E_2$. Adsorption of analyte also can occur at $E_3$ and for long $t_3$ the concentration of analyte at the electrode surface is reestablished to the value of the bulk solution ($C^s = C^b$). The analytical application of this method, now known as Pulsed Amperometric Detection (PAD), has been demonstrated for alcohols, polyalcohols and carbohydrates (reducing and non-reducing) (1-6); amines and amino acids (primary and secondary) (7); aminoglycosides (8); and numerous sulfur compounds (except sulfate, sulfonic acids and sulfones) (9-11).

Recently, Pulsed Coulometric Detection (PCD) was described (12). The significant difference between PAD and PCD lies in the instrumental protocol related to measurement of the faradaic signal. In PAD, electrode current is averaged over a time period of 16.7 ms (i.e., 1/60 $Hz^{-1}$) whereas in PCD the amperometric response is electronically integrated over an integral number of sequential 16.7-ms periods (12). PCD inherently has a larger signal-to-noise ratio (S/N) because of the larger signal strength and because the integral of a 60-Hz correlated noise signal, a predominant form of noise in electronic instrumentation, remains at zero over the integration period.

With the advent of more complex liquid chromatographic techniques which employ a variety of gradient elution methods, it is necessary to develop detectors which are capable of sustaining high values of sensitivity and detectability over the gradient period, and which also can reject automatically the accompanying variation in background signal. Detectors traditionally used for aliphatic compounds cannot be used in pH-gradient liquid chromatography (LC) because they are affected by changes in ionic strength. Photometric detection suffers because of an inherently low sensitivity for aliphatic compounds without extensive $\pi$-bonding and because of baseline drift which accompanies a change in the refractive index of the mobile phase. Refractive index detection is strongly affected by concentration gradients and the baseline shift observed for even small changes in mobile phase composition can overwhelm the analyte signal.

The methods of PAD (1–10) and PCD (12) were introduced for detection of numerous aliphatic organic compounds in conjunction with liquid chromatography (LC). However, the ability of either technique to resist even a slight pH change is strongly dependent on the detection potential and the electrode material selected. In fact, PAD at a Pt electrode in a flow-injection (FI) system has been suggested for the determination of pH changes in caustic media (13). Sensitivity of the baseline in PAD and PCD to changes in solution pH is greatest for amines and sulfur compounds at Au and Pt because the anodic detection reactions are catalyzed by simultaneous formation of surface oxide on the noble metal electrodes (7,9,10).

SUMMARY OF THE INVENTION

It is an object of the present invention to provide an improved pulsed coulometric detection method. Briefly, the pulsed coulometric detection method according to the present invention is intended for use in electrochemical modes of detection which utilize anodic cleaning and cathodic reactivation of electrode surfaces in a liquid chromatographic environment.

In one preferred embodiment, the method comprises the steps of generating multi-step potential waveforms having cyclic potential changes where the cyclic waveforms have a first initial potential value ($E_1$) for a first time period $t_d$ so that the electrode surfaces exist in an oxide-free state, advancing (increasing) the potential value to a second, higher value ($E_{1'}$) for a time period $t_s$ so as to cause the formation of surface oxide with concurrent electrocatalytic oxidative reaction of soluble and/or adsorbed analyte, and returning the potential value to said first value $E_1$ for a holding time period $t_h$, during which all oxide formed during the potential change to $E_{1'}$ is cathodically stripped from said electrode surfaces.

Other objects and features of the present invention will become apparent from the following detailed description when taken in conjunction with the accompanying drawings.

BRIEF DESCRIPTION OF THE DRAWINGS

FIGS. 3A and 3B. Current-potential and charge-potential response for thiourea at the Au RDE in 0.25 M $NH_4NO_3$ (pH 5.1).
Solutions: (A,C) blank, (B,D) 100 $\mu$M thiourea.
Curves: (A,B) current vs. potential (i-E), (C,D) charge vs. potential (q-E).

Injections: 100-µL of 100 µM thiourea in 0.25 M NH$_4$NO$_3$.
Waveforms: (PS-PCD) WF-3, (PCD) WF-2, (PAD) WF-1.

Figure 6:
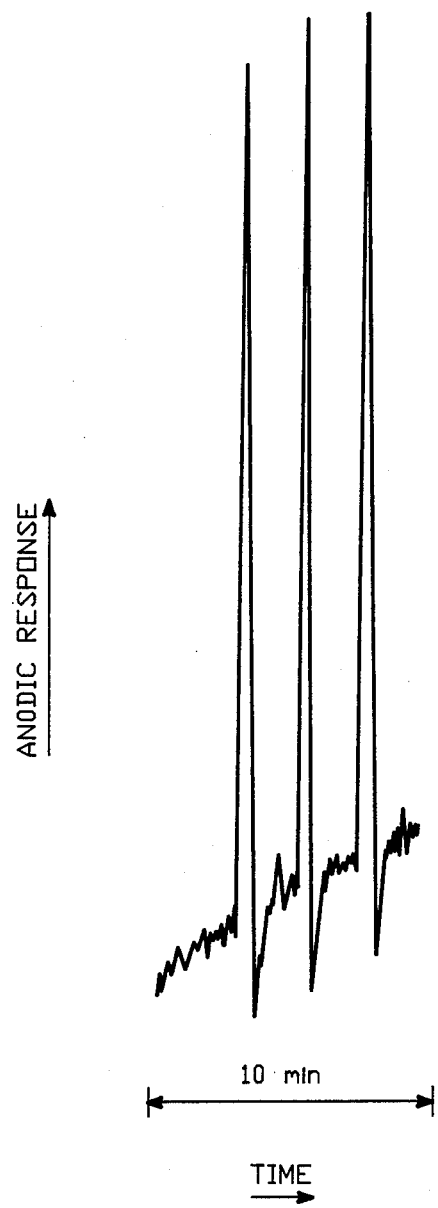

FIG. 6. Demonstration of post-peak dips for detection of thiourea by PAD in 0.25 M NH$_4$NO$_3$ (pH 5.1).
Injections: 100 µM thiourea in 0.25 M NH$_4$NO$_3$.
Waveform: WF-1.

Figure 7B:
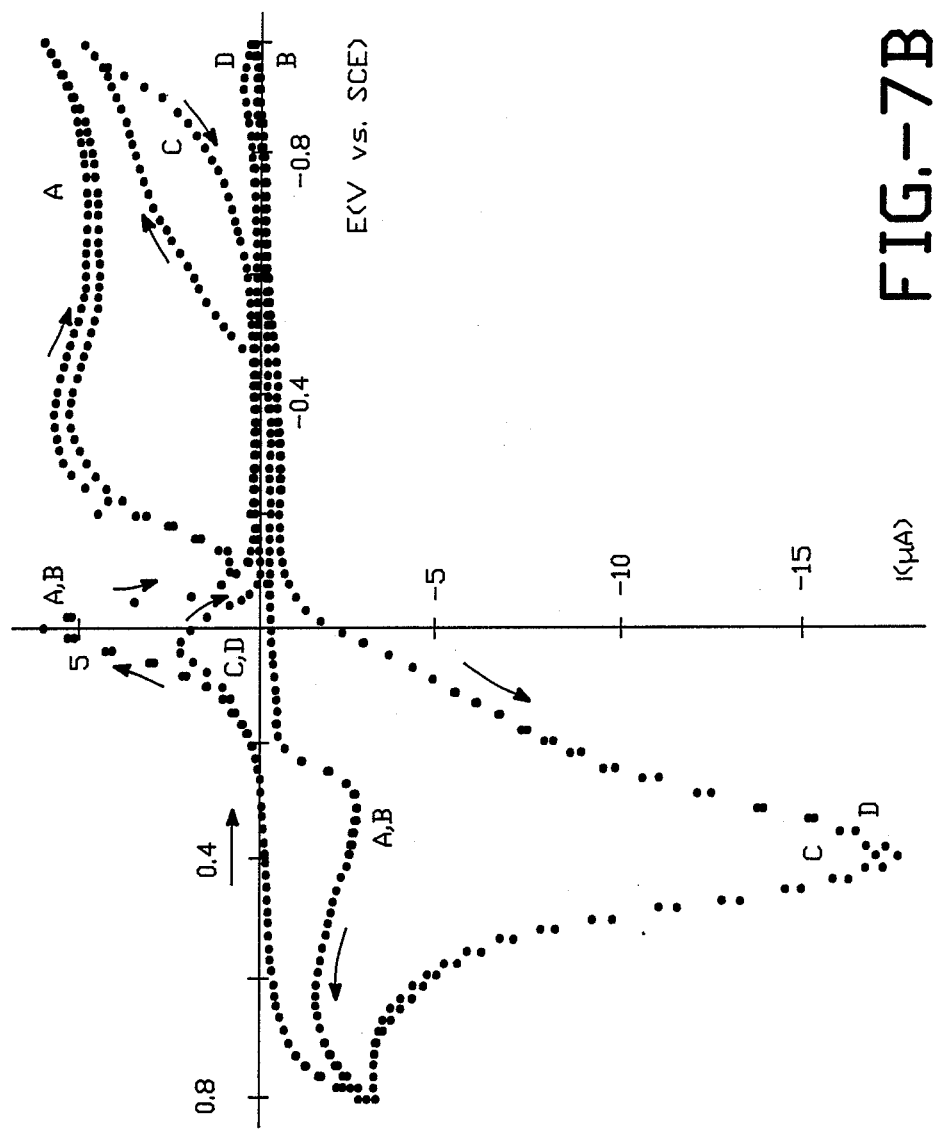

FIGS. 7A and 7B. Current-potential curves for thiourea at a Au RDE vs. solution pH.
Solutions: (A) 0.25 M NH$_4$NO$_3$ (pH 5.1), (B) 0.20 M NaOH (pH ca. 13).
Curves: (A,C) air sat'd. (B,D) N$_2$ sat'd. (A,B) blank, (C,D) 0.20 mM thiourea.

Figure 8:
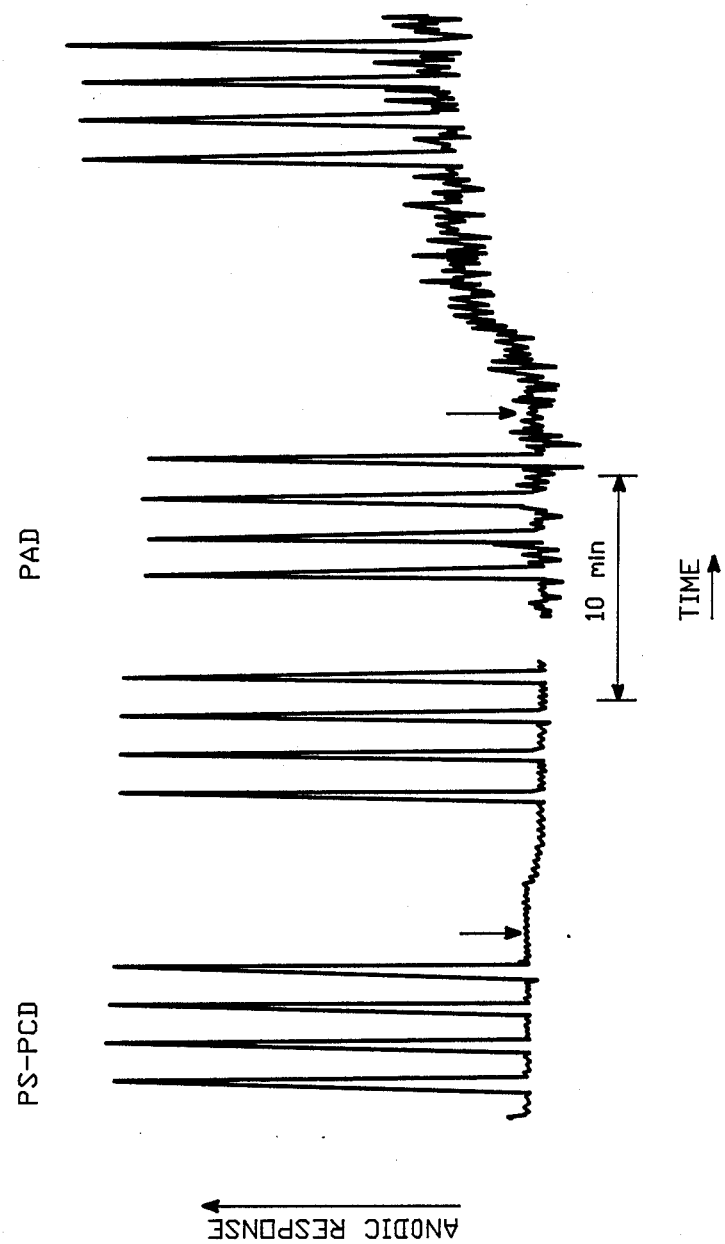

FIG. 8. Comparison of baseline shift for detection of thiourea in NH$_4$NO$_3$ by PS-PCD and PAD with a pH change from 3.8 to 5.1 (marked by arrow).
Injections: 100 µM thiourea in 0.25 M NH$_4$NO$_3$.
Waveforms: (PS-PCD) WF-3, (PAD) WF-1.

FIG. 9A and 9B. Response for glucose at the Au RDE in 0.20 M NaOH (pH ca. 13).
Solutions: (A,C) blank, (B,D) 1.0 mM glucose.
Curves: (A,B) current vs. potential (i-E), (C,D) charge vs. potential (q-E).

Figure 10:
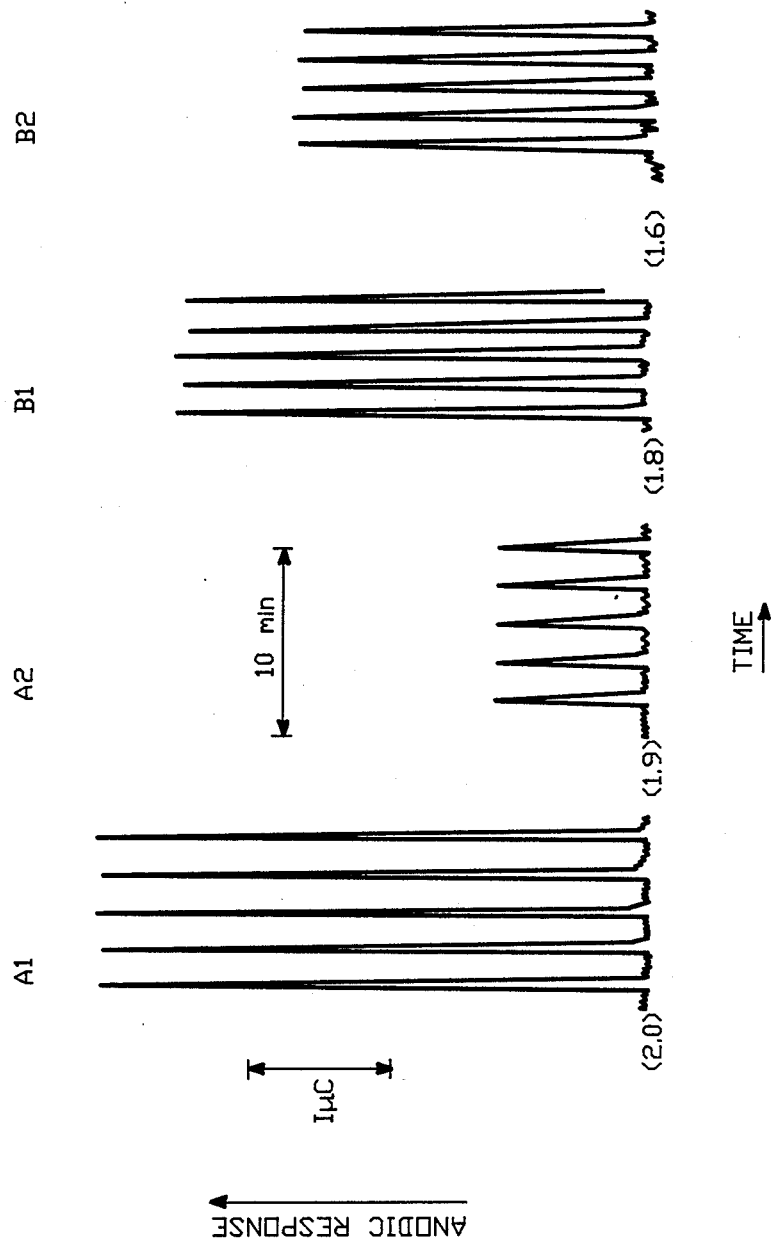

FIG. 10. Comparison of flow-injection peaks for glucose and thiourea by PS-PCD with waveforms of FIG. 1.
Solutions: (A1, A2) 0.20 mM glucose in 0.20 M NaOH
(B1,B2) 0.10 mM thiourea in 0.20 M NaOH
Waveforms: (A1) WF-4, (A2) WF-5,1. (B1) WF-4, (B2) WF-5.

Figure 11:
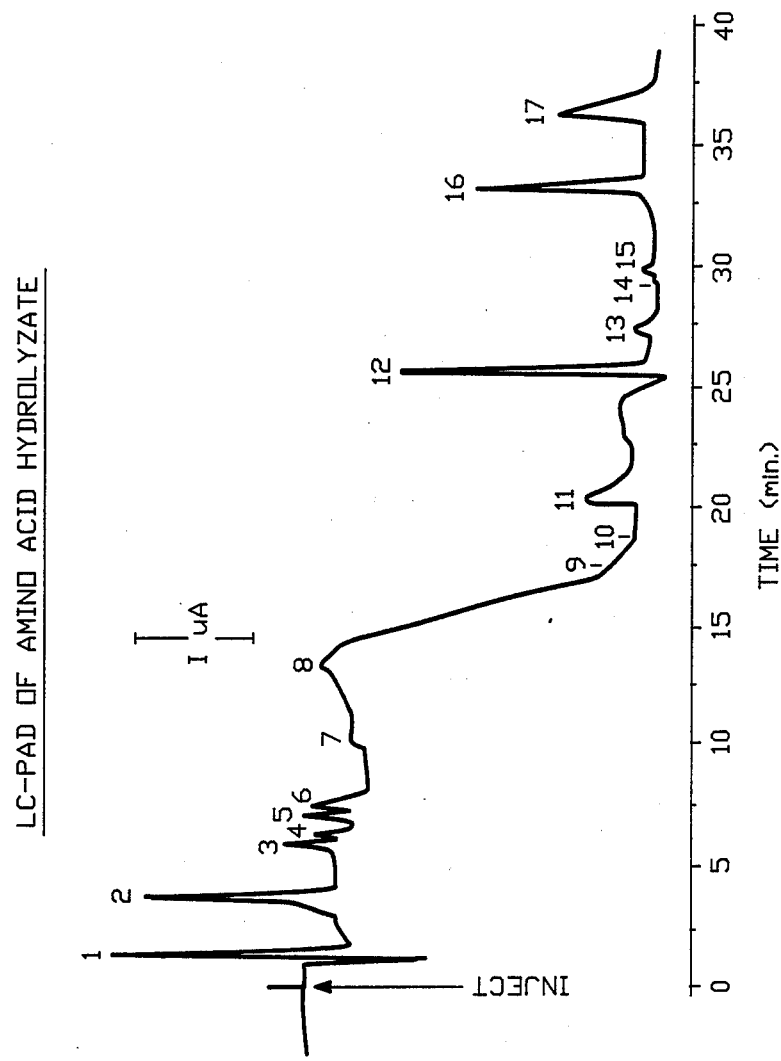

FIG. 11. Gradient liquid chromatographic separation and PAD using a pH reference of a complex mixture of amino acids.

Figure 12:
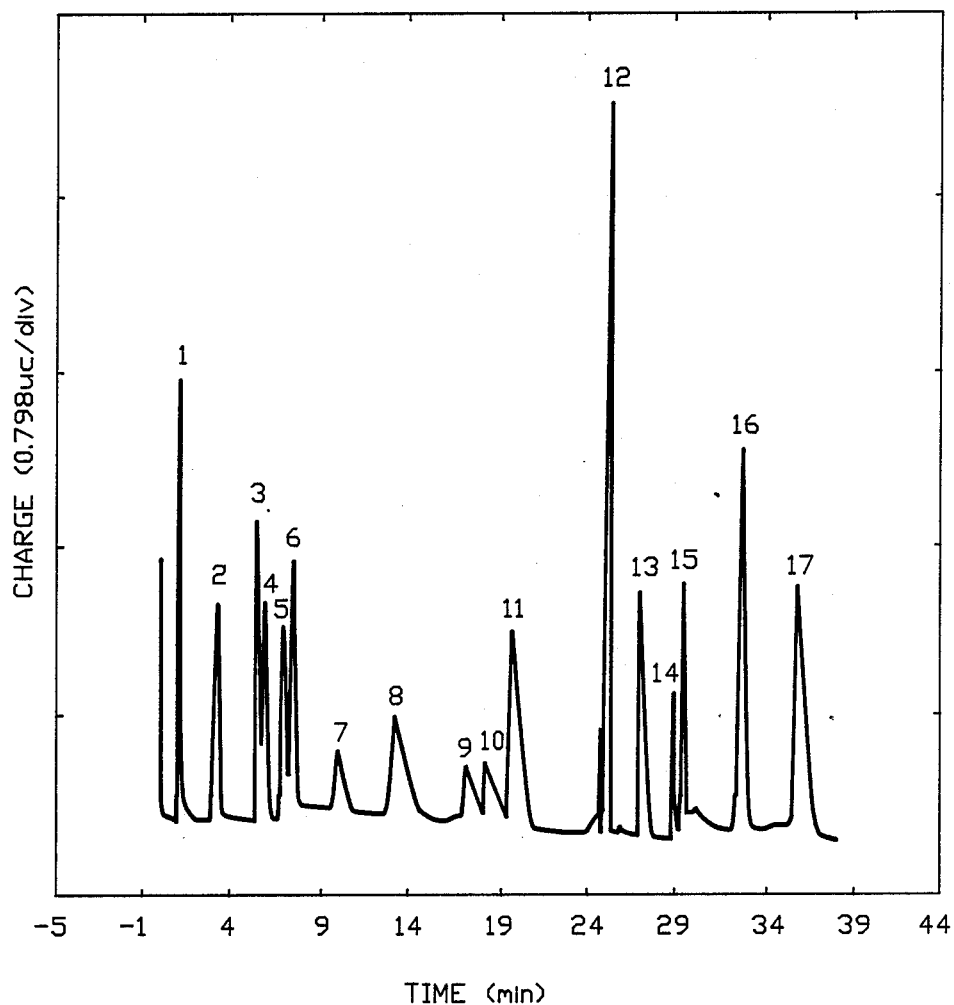

FIG. 12. Similar to FIG. 11 except for using PS-PCD.

Figure 13:
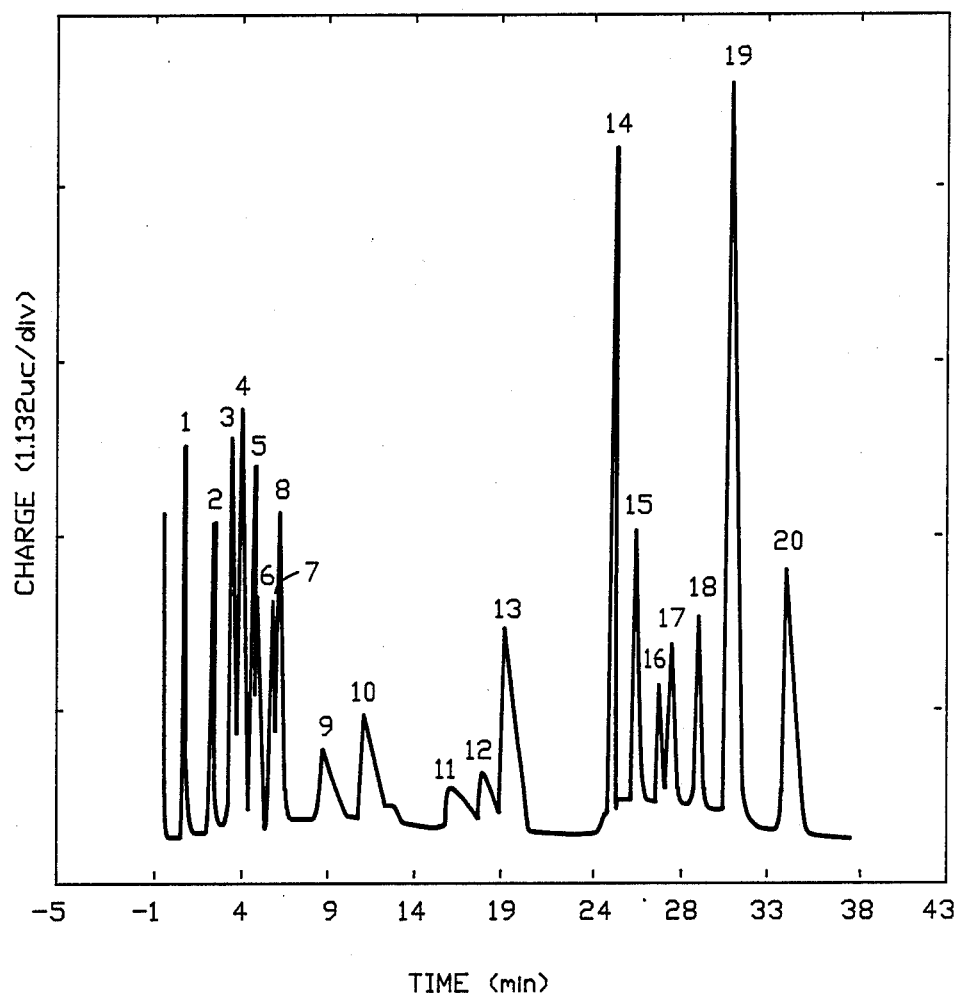

FIG. 13. Similar to FIG. 12 with improved chromatography.

Figure 14:
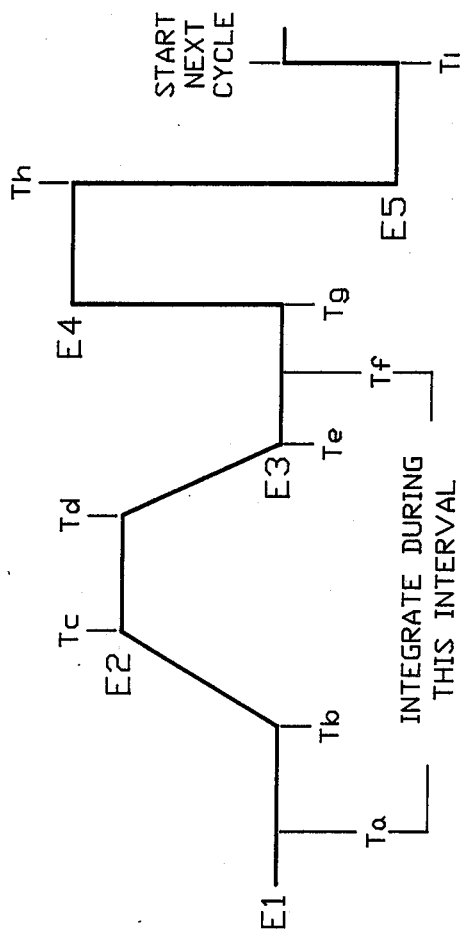

FIG. 14. Potential waveform used in connection with separation process of FIGS. 12 and 13.

DETAILED DESCRIPTION OF THE DRAWINGS

An improved variation of PCD will now be described in which the detection potential in the pulsed waveform is varied in a cyclic fashion during current integration. The cyclic potential change may be according to potential-sweep or potential-step functions, or a combination thereof, and the abbreviation PS-PCD is applied for the technique. The greatest significance for PS-PCD is anticipated for anodic detections based on oxide-catalyzed reactions, and it has been concluded that the technique is capable of virtual rejection of baseline drift in LC methods utilizing pH-gradient elution. The theory of gradient elution is well known and is described, for example, by Snyder and Kirkland in Introduction to Modern Liquid Chromatography, Second Edition, John Wiley & Sons, Inc. (1979), pp. 663–715, the details of which are hereby incorporated by reference.

Figures 1A, 1B, 1C, 1D:
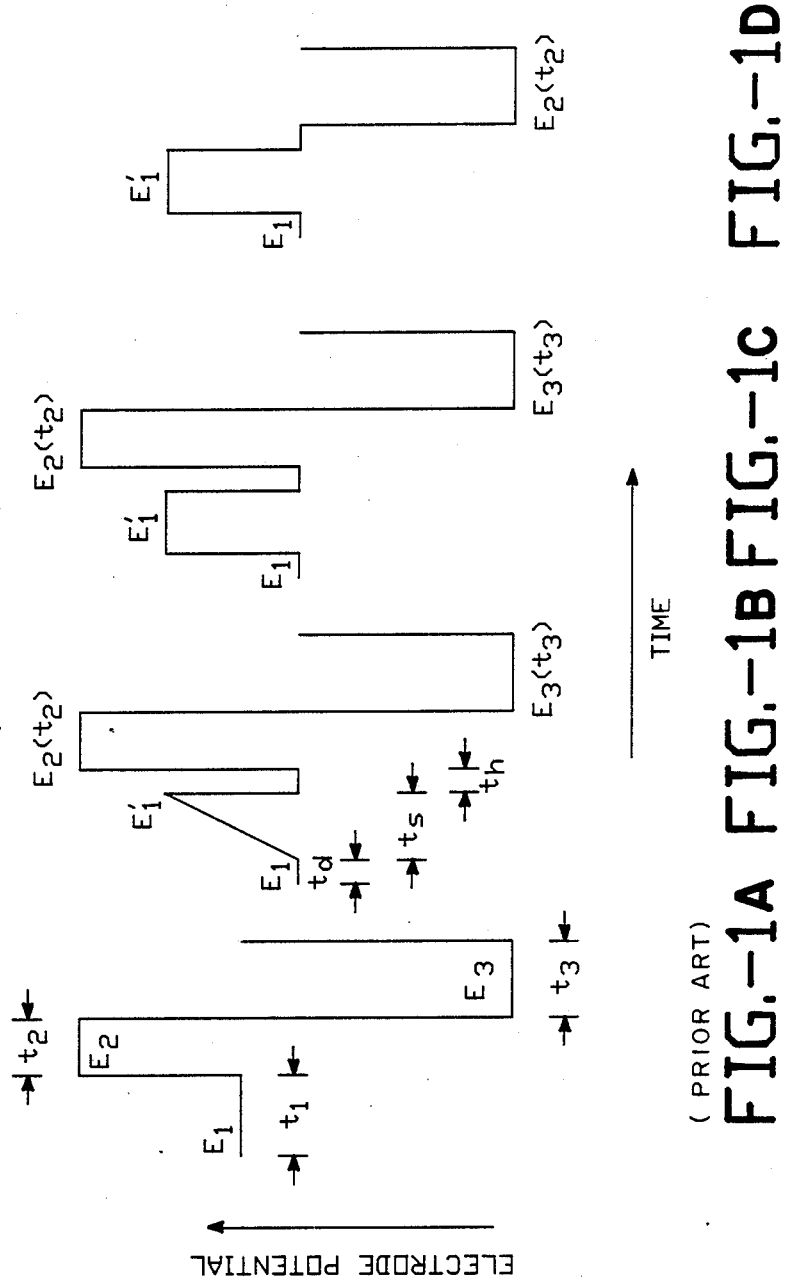
FIGS. 1A, 1B, 1C and 1D. Potential-time waveforms. (A) PAD (B-D) PS-PCD.

Typical potential waveforms for PS-PCD are shown in FIGS. 1B and 1C for comparison to the conventional waveform for PAD and PCD in FIG. 1A. In PS-PCD, the initial value of $E_1$ is chosen so that the electrode surface exists in an oxide-free state. Following a delay time of $t_d$, the detection potential is advanced to the value $E_{1'}$ by a fast potential sweep (FIG. 1B) or a potential step (FIG. 1C) for a time period of $t_s$. The value of $E_{1'}$ is chosen to cause the formation of surface oxide with the concurrent electrocatalytic oxidative reaction of soluble and/or adsorbed analyte. The detection potential then is returned to the initial value $E_1$ for the holding period $t_h$ during which all oxide formed during the potential change to $E_{1'}$ is cathodically stripped from the electrode surface. The total time of the detection period is $t_1 = t_d + t_s + t_h$. An integrator (analog or digital) is activated during period $t_d$ and remains active throughout period $t_H$. The output signal from the integrator is sampled at the end of period $t_h$ and the value, or a proportional value, is fed to a recording device. Thereafter can be applied the positive and negative pulses to $E_2$ and $E_3$ which achieve anodic cleaning and cathodic reactivation, respectively. The integrator is reset to zero at the end of period $t_3$ just prior to the start of the next waveform cycle.

Background rejection in PS-PCD is achieved because the anodic charge for surface oxide formation ($q_{a,ox}$) during the potential change from $E_1$ to $E_{1'}$ is automatically compensated by the cathodic charge for oxide reduction ($q_{c,ox}$) with the potential change from $E_{1'}$ to $E_1$. Background rejection is exact if $q_{c,ox} = -q_{a,ox}$. Sensitivity for analyte detection is greatest if the process is irreversible, i.e., no cathodic signal is obtained for reduction at $E_1$ of the products of the anodic detection reaction at $E_{1'}$. The value $E_{1'}$ is chosen to maximize the extent of oxidative reaction of soluble and absorbed analyte. However, $E_{1'}$ should not be so large positive to cause significant anodic solvent breakdown with evolution of $O_2$.

For the PS-PCD waveforms in FIGS. 1B and 1C, the values of $E_{1'}$ and $t_s$ can be sufficiently large to provide complete oxidative cleaning of the electrode and a subsequent step to $E_2$ for further oxidative cleaning may not be needed. The resulting waveform is shown in FIG. 1D. Advantages include a higher waveform frequency.

EXPERIMENTAL SECTION

Chemicals

Solutions were prepared from Reagent Grade Chemicals (Fisher Scientific, Fair Lawn, N.J.) and purified water (NANOpure II, Barnlsted Co., Boston, Mass.). Except where noted in voltammetric experiments, dissolved $O_2$ was removed by purging with pure $N_2$.

Instrumentation

All data were obtained with a potentiostat (PAR 174A, EG&G Princeton Applied Research Corporation, Princeton, N.J.) under computer control (Hewlett Packard, Palo Alto, Calif.) (5,12). The definitions of waveforms, as well as all other timing and switching operations, were under software control. The flow-injection (FI) system was based on a peristaltic pump (Minipuls HP4, Gilson Medical Electronics, Middleton, Wis.) and Teflon connecting tubing. The sample volumes injected were 100 µl and the flow rate was 0.5 ml min$^{-1}$. The electrochemical flow-through cell was of the "thin-layer" design (Dionex Corporation, Sunnyvale, Calif.) with a Au electrode (ca. 0.005 cm$^2$). A saturated calomel reference electrode (SCE) was substituted for the manufacturer supplied Ag/AgCl electrode (SSCE) Voltammetry was performed at a Au rotated disk electrode (RDE, 0.0050 cm$^2$) in a MSR rotator (Pine Instrument Co., Grove City, Pa.).

Procedures

Voltammetry at the Au RDE was performed using a staircase waveform in which 20-mV steps were applied to the Model 174A to simulate a scan rate of ca. 4.8 V min$^{-1}$. Electrode current was measured during the last 16.7 ms of the time period for each step. Charge-potential (q-E) plots were obtained during staircase scans by continuous analog integration of electrode current.

The potential sweep from $E_1$ to $E_{1'}$ in waveform of FIG. 1B for PS-PCD was simulated by a staircase waveform using 30 mV steps initiated at the end of the delay time $t_d$. The detection response for the waveforms in FIGS. 1C and 1D were found to be nearly equivalent to that in FIG. 1B for sulfur compounds. Hence, the waveform in FIG. 1D was used to obtain most of the PS-PCD data shown here. For waveforms shown in FIGS. 1B-1D, the integrator was activated at the start of period $t_1$. The sampling of electrode current in PAD and the accumulated charge in PCD and PS-PCD was achieved during a 16.7 msec period at the end of the detection period $t_1$. Detailed descriptions of the waveforms used to obtain data presented here are given in Table I.

RESULTS AND DISCUSSION

Staircase Voltammetry with Current Integration

Sulfur compounds exhibit an anodic behavior at noble-metal electrodes which is under strong control by the simultaneous anodic formation of surface oxide (9,10). This response is typified by the i-E plots shown in FIG. 2 (Curves B-D) which were obtained by staircase voltammetry obtained at a Au RDE rotated at 900 rev min$^{-1}$ in 0.25 M NH$_4$NO$_3$ (pH 5.1) as a function of thiourea concentration. For comparison, the residual i-E plot obtained in the absence of thiourea is shown (Curve A). The surface-catalyzed anodic detection of thiourea is observed to occur simultaneously with the formation of surface oxide during the positive potential sweep in the region ca. 0.6-1.3 V. Anodic solvent breakdown with evolution of O$_2$ occurs at Au electrodes for E>ca. 1.3 V at pH 5.1. The anodic signal for thiourea decreases to zero on the negative sweep from 1.5 V when the rate of oxide formation goes to zero. Clearly, thiourea is reactive only with simultaneous formation of surface oxide and the oxide-covered Au electrode is inert for further anodic reaction of thiourea. The surface oxide formed during the positive potential sweep is cathodically reduced on the subsequent negative sweep to produce the cathodic peak in the region 0.5-0.2 V at pH 5.1. 0364 The optimum detection potential for PAD and PCD ($E_1$ in FIG. 1A) applied for thiourea at pH 5.1 in FI or LC systems is in the range ca. 1.0-1.2 V, based on the appearance of a peak value for the anodic signal in the i-E plots of FIG. 2. For these values of detection potential, however, a large simultaneous background signal is obtained in PAD and PCD as a result of the formation of surface oxide.

The concept of PS-PCD is demonstrated for a slow triangular staircase potential sweep (4.8 V min$^{-1}$) at the Au RDE by the charge-potential (q-E) plots in FIG. 3 (curves C and D). The simultaneous i-E data (curves A and B) obtained by staircase voltammetry are shown also to aid in the interpretation. The rotation speed was 1600 rev. min$^{-1}$. In the residual q-E plot for the absence of thiourea (curve C), a rapid buildup of charge occurs when oxide formation is initiated at ca. 0.7 V on the positive sweep and the accumulated charge returns to ca. zero starting at ca. 0.5 V on the negative sweep when the surface oxide is cathodically dissolved. In the presence of thiourea (curve D), the net charge remaining on the integrator after completion of the cyclic potential sweep corresponds to the contribution from the anodic reaction of thiourea

Rate of Baseline Equilibration

The potential waveforms for PS-PCD (FIGS. 1B-1D) incorporate a sampling methodology that can result in virtual rejection of the large background signals from oxide formation commonly observed in PAD and PCD. The anodic charge from oxide formation ($q_{a,ox}$) accumulated during the positive potential change from $E_1$ to $E_{1'}$ is compensated by the nearly equivalent but opposite charge from the cathodic dissolution of the oxide ($q_{c,ox}$) for return of the potential from $E_{1'}$ to $E_1$.

Figure 4:
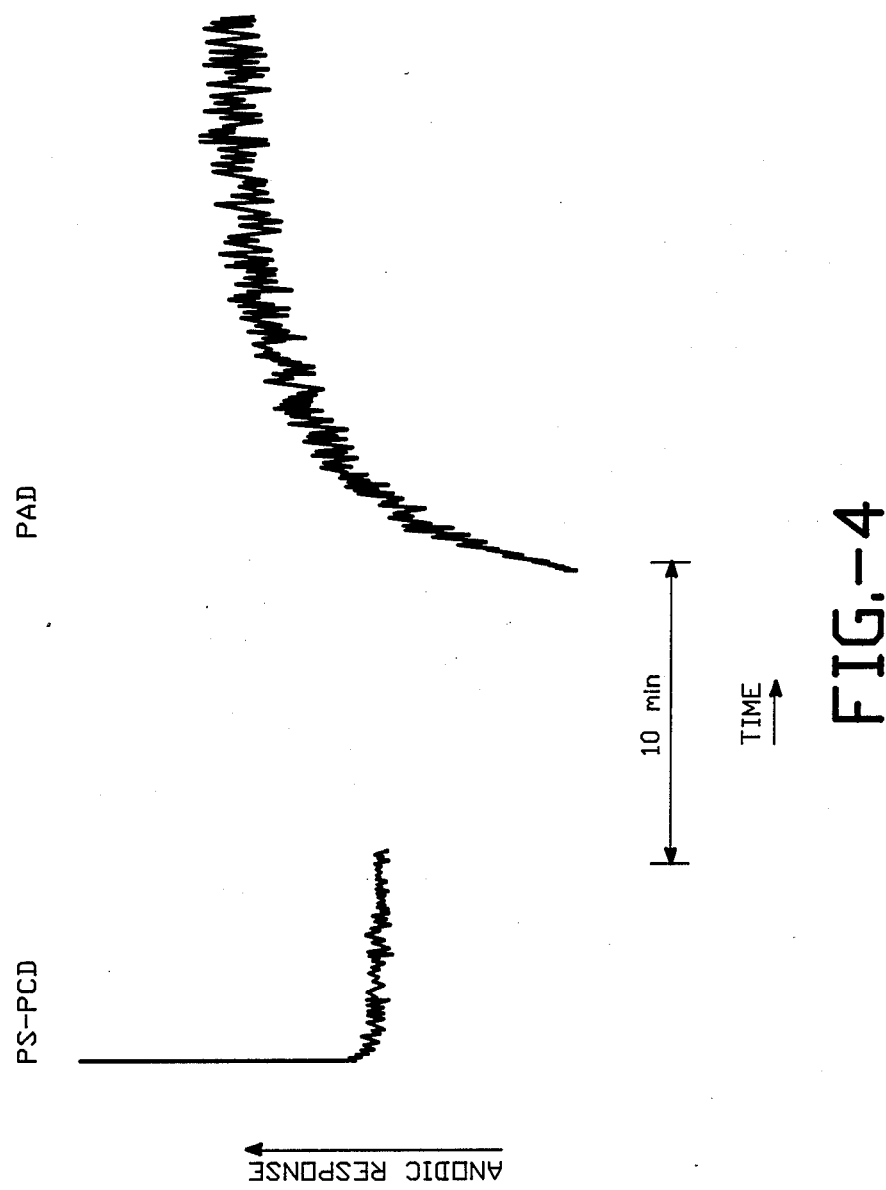
FIG. 4. Comparison of settling time and drift for PS-PCD and PAD in 0.25 M $NH_4NO_3$ (pH 5.1). Waveforms: (PS-PCD) WF-3, (PAD) WF-1.

The rate of equilibration and the drift of the baseline are compared in FIG. 4 for PS-PCD and PAD at a Au electrode in the FI system. The Au electrode was polished (0.5 μm alumina) prior to recording each response curve. The zero current for PAD is off the scale of FIG. 4. It is seen that severe baseline drift in PAD continues for longer than 10 min. This results from the gradual increase in the true electrode area during the detection process due to surface reconstruction caused by the repeated cycles of oxide formation and dissolution. With baseline rejection in PS-PCD, there is virtually no consequence evident from a change in electrode surface area. Commonly for PS-PCD, the baseline is observed to reach its "zero" value within ca. 5-10 cycles of the waveform applied to a freshly polished electrode, as demonstrated in FIG. 4. Furthermore, deviation from this value over a several-hour period is less than or equivalent to the magnitude of the high frequency noise shown on the background signal. The equilibration rate and the extent of baseline drift for PS-PCD are virtually independent of the state of the electrode, i.e., whether the electrode has been "well-worked" or freshly polished. It is not necessary to polish electrodes used in PAD, PCD or PS-PCD. Electrodes can become very "tarnished" in appearance because of surface reconstruction after many months of operation; however, their response is not degraded.

Figure 5:
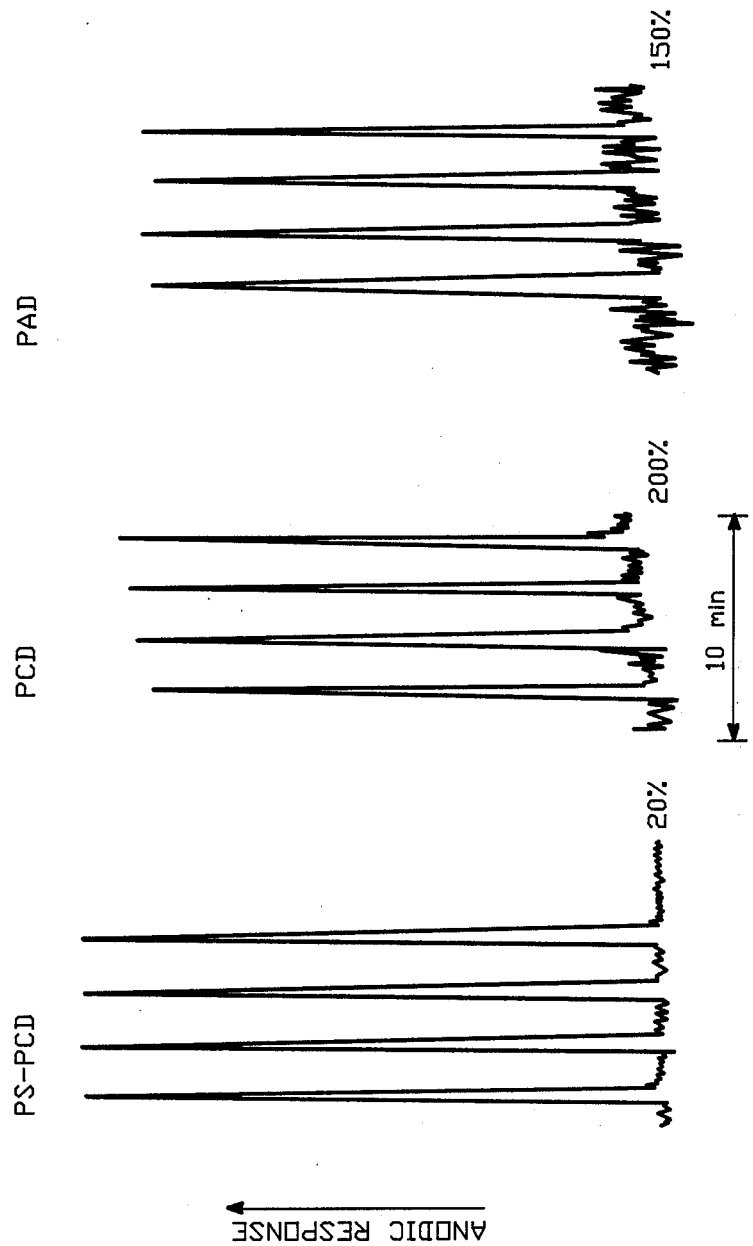
FIG. 5. Comparison of detection peaks and baseline offset for PS-PCD and PAD in 0.25 M $NH_4NO_3$ (pH 5.1).

A comparison is shown in FIG. 5 of the detection peaks for thiourea in 0.25 M NH$_4$NO$_3$ (pH 5.1) obtained by PSPCD, PCD and PAD in the FI system. The full-scale current sensitivity of the stripchart recorder was adjusted for each detection mode so that the peak deflections would be equivalent. This allows for direct visual comparison of S/N factors in the figure. The magnitude of the baseline response is represented in the figure as a percentage of the net peak response. For example, the baseline signal for PS-PCD is only ca. 20% of the peak height for injections of 100 μM thiourea, whereas the baseline signal for PAD is nearly 150% the peak height. A small uncompensated baseline offset can persist in PS-PCD for three reasons: potential and current offsets in the operational amplifiers of the electronic instrument; a very short period for the second application of $E_1$ (i.e., period $t_h$), which does not permit complete cathodic removal of all surface oxide; and choice of an electrode material, electrode potentials ($E_1$ and $E_{1'}$ in FIG. 1B), and/or solution conditions for which $q_{c,ox} \neq -q_{a,ox}$.

Limits of Detection and Analytical Calibration

The detection limits for PS-PCD of sulfur compounds are superior to PAD and PCD, as would be anticipated from observation of the respective S/N values estimated from FIG. 5. The limit of detection (LOD) for thiourea by PS-PCD (S/N=3) was determined by flow injection to be ca. 2 $\mu M$ for waveform WF-3 (see Table I), which corresponds to 15 ng in a 100-$\mu l$ sample (0.15 ppm). The LOD for PAD (waveform WF-1) was 15 $\mu M$ (110 ng, 1.1 ppm) and the LOD for PCD (waveform WF-2) was 6 $\mu M$ (45 ng, 0.44 ppm). The calibration curve for PS-PCD was linear over two decades in concentration (i.e., 2–200 $\mu M$). Note that the detection limits for PAD and PCD using the present "home-built" instrument are poorer than can be achieved using commercial instrumentation (Dionex Corp.). Hence, the values of LOD given here should be considered only for purposes of intercomparison of the three detection modes and not as indicators of values of LOD expected from state-of-the-art instrumentation.

Baseline Estimation in Flow-Injection Determinations

Figure 2:
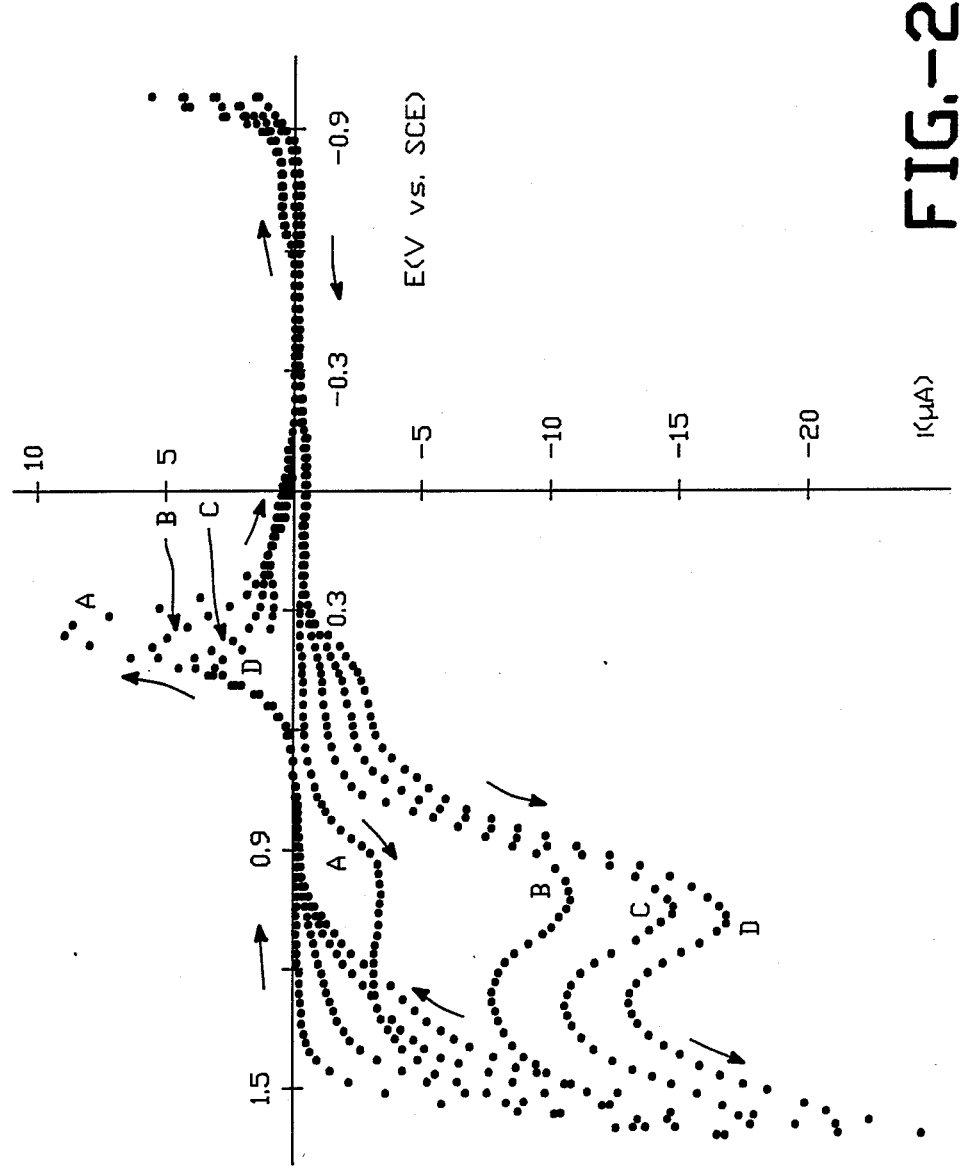
FIG. 2. Current-potential response for thiourea at a Au RDE in 0.25 M $NH_4NO_3$ (pH 5.1). Concentration (mM): (A) 0.0, (B) 0.10, (C) 0.30, (D) 0.50.

Current-potential curves obtained by staircase voltammetry at the Au RDE were shown in FIG. 2 as a function of thiourea concentration. Clearly, the apparent peak signal observed for cathodic dissolution of surface oxide ($q_{c,ox}$) decreases as thiourea concentration is increased. This is concluded to occur because the rate of oxide formation is inhibited substantially by the presence of adsorbed sulfur and/or thiourea with the result that a smaller amount of surface oxide is produced during the positive potential sweep. This fact can have serious effects on the interpretation of i-t plots obtained for applications of PAD or PCD to flow-injection or chromatographic systems. The true baseline corresponding to the detection peak is not correctly estimated by extrapolation of the baseline observed immediately before or after the detection peak. Evidence of this effect is the appearance of the postpeak dips shown in FIG. 6 for injections of 100 $\mu M$ thiourea. This demonstrates not only that less surface oxide is formed in the presence of adsorbed thiourea, but also that a finite amount of time (i.e., several waveform cycles) is required to completely clean and reactivate the electrode surface following passage of the sample bolus through the detector cell. For PS-PCD, there is no consequence of the variation in surface oxide coverage since the oxide formed as a result of the change from $E_1$ to $E_{1'}$ is subsequently cathodically dissolved following the potential change from $E_{1'}$ back to $E_1$ and the net integrated signal for this cyclic process remains at virtual zero regardless of changes in $q_{a,ox}$.

Effect of pH Change

To achieve minimal baseline in PS-PCD, it is essential that $E_1$ corresponds to a value at which the electrode is free of oxide and dissolved $O_2$ is not detected. Staircase voltammograms obtained at the Au RDE at 1600 rev min$^{-1}$ are shown in FIG. 7A for thiourea in 0.25 M NH$_4$NO$_3$ (pH 5.1) and in FIG. 7B for 0.20 M NaOH (pH ca. 13). As a result of the change in pH from 5.1 to 13, the peak potential for oxide stripping at the Au electrode shifts negative by ca. 0.40 V, whereas the half-wave potential for $O_2$ reduction shifts by only ca. 0.15 V. Hence, for high values of pH, it becomes impossible to locate a value for $E_1$ in the PS-PCD waveform (FIGS. 1B–1D) such that all surface oxide is cathodically dissolved but for which dissolved $O_2$ is not detected. The value −0.15 V at pH 13 is only marginally successful, and application of PS-PCD to Au electrodes in alkaline solutions containing dissolved $O_2$ is limited to pH<ca. 13.

It is important also that the range of the potential change from $E_1$ to $E_{1'}$ is chosen to span the majority of the voltammetric region for surface oxide formation; however, $E_{1'}$ should not exceed values for onset of significant evolution of $O_2$. From the i-E curves in FIG. 7, it is observed that the onset of anodic $O_2$ evolution is shifted negative by ca. 0.40 V for the change in pH from 5 to 13. Clearly, it is impossible to design a waveform for successful PS-PCD at pH 5 which will apply satisfactorily at pH 13 without adjustment of all values of potential in the waveform.

Peaks for thiourea obtained by PS-PCD and PAD are compared in FIG. 8 for flow-injection detections with a pH step in the carrier solution from 3.8 to 5.1, as designated by the arrow. The recorder setting for each experiment was adjusted such that the peak deflection would be nearly equivalent for the two detection techniques. For PS-PCD, the change in baseline response is very small, whereas the baseline shift for PAD is much more severe. The sensitivity for thiourea detection by either method exhibits little variation with the change in solution pH. Also, it is readily apparent that the S/N is superior for PS-PCD.

Consideration of Carbohydrate Detection

Monosaccharides and disaccharides exhibit a nearly mass transport-limited peak-shaped response at a Au electrode in alkaline solutions. (5). As shown for the positive potential sweep in the voltammetric curves in FIG. 9 obtained at the Au RDE at 900 rev min$^{-1}$, the anodic peak for glucose is obtained in a potential region where no substantial quantity of surface oxide is formed (compare curves A and B). Even though the voltammetric peak response for glucose is virtually mass-transport controlled, detection at a constant potential without the benefit of the cleaning, and activation pulses in PAD or PCD is unsatisfactory. For detection at constant potential, the anodic response for carbohydrates decays steadily at Au electrodes. The loss of surface activity is concluded to be the result of the accumulation of adsorbed products of the detection reaction. A similar observation at Pt electrodes led to the original motivation for the development of PAD (1). As shown by curve B in FIG. 9 (positive sweep), oxidation of the carbohydrate ceases concurrently with the onset of oxide formation at ca. 0.2 V. The peak signal superimposed on the oxide formation wave (0.25–0.5 V) in the presence of carbohydrates corresponds to the oxide-catalyzed oxidative desorption of the adsorbed carbonaceous material. The basis of PS-PCD for carbohydrates is illustrated by the Q-E plots for glucose in FIG. 9 (curves C and D) obtained with the slow triangular staircase sweep (4.8 V min$^{-1}$).

For carbohydrates under highly alkaline conditions, it is not possible to choose values of $E_1$ and $E_{1'}$ which encompass the entire detection peak without the simultaneous detection of dissolved $O_2$. This observation, plus the knowledge that a minimal background current is observed in determinations of carbohydrates by PAD and PCD, because oxide is not formed at the detection potential, leads to the conclusion that there is not likely to be a significant improvement in detectability for carbohydrates by PS-PCD in comparison to PCD in solutions of pH>ca. 11. Furthermore, sensitivity for carbohydrates decreases rapidly for pH<11.

Comparison of Waveforms

The optimization of the waveform for PS-PCD, e.g., choice of FIG. 1B vs. FIGS. 1C or 1D, is influenced by the analyte(s) of interest For analytes whose detection is inhibited by formation of surface oxide, e.g., carbohydrates (see FIGS. 9A and 9B), the waveform depicted in FIGS. 1C and 1D are not considered appropriate because the stepwise change of potential from $E_1$ to $E_{1'}$ results in the rapid and extensive formation of oxide with cessation of analytical response (see FIG. 9). Adsorbed analytes detected by mechanisms which are catalyzed by formation of surface oxide, e.g., sulfur compounds, are expected to be detected well by either waveform. Results from a comparison of the waveforms in FIGS. 1B and 1D are shown in FIG. 10 for detection of glucose (A1, A2) and thiourea (B1, B2) in 0.2 M NaOH. For the comparison, the total period of detection was the same in the two waveforms (1000 ms). Numerical values for the baseline signal ($\mu C$) are indicated in parentheses. Glucose shows a substantially higher sensitivity for the waveform in FIG. 1B as compared to FIG. 1D, as predicted. Thiourea is detected with similar sensitivity, also as predicted. As was the case for thiourea, amino acids also are detected by processes which are catalyzed by the formation of the surface oxides, as will be described in conjunction with FIGS. 11-13.

FIG. 11 contains a chromatogram for 17 amino acids (peak identity given on the next page of the enclosure) using the Dionex scheme for gradient elution with detection by PS-PCD. The chromatographic column was the Dionex AS-8. The tremendous shift in baseline is typical for PAD or PCD detection of amino acids when the gradient elution method is used, i.e., the composition of the mobile phase is caused to change during the elution process. Note it is apparent that some of the detection peaks are lost in the shifting baseline. This particular chromatogram was obtained using the pH electrode as the reference. If the SCE reference had been used, the baseline shift would have been even more severe.

The peaks of FIG. 11 are shown below:
Anion-exchange LC-PAD of the Pierce protein hydrolyzate
Electrode: Au, glass reference
Column: AS-8
Solutions: See Table III
Samples: Pierce protein hydrolyzate, $5 \times 10^{-4}$ M each except cystine at $2.5 \times 10^{-4}$ M

| (1) arginine | (10) leucine |
| (2) lysine | (11) methionine |
| (3) threonine | (12) histidine |
| (4) alanine | (13) phenylalanine |
| (5) glycine | (14) glutamic acide |
| (6) serine | (15) aspartic acid |
| (7) valine | (16) cystine |
| (8) proline | (17) tyrosine |
| (9) isoleucine | |

Waveform:

$E_1 = 750$ mv, 300 ms $E_2 = 1000$ mv, 100 ms $E_3 = -350$ mv, 100 ms

FIG. 12 contains a chromatogram obtained under the exact conditions of FIG. 11 except that PS-PCD was used for detection, with the pH reference. It is very evident that the great significance of the invention is the stability of the baseline when gradient elution is employed.

The peaks of FIG. 12 are identified as follows: LCL-PCD of the pierce protein hydrolyzate using a glass reference electrode
Electrode: Au, glass reference
Column: AS-8
Solutions: See Table III
Samples: Pierce protein hydrolyzate, $5 \times 10^{-4}$ M each, except cystine at $2.5 \times 10^{-4}$ M

| (1) arginine | (10) leucine |
| (2) lysine | (11) methionine |
| (3) threonine | (12) histidine |
| (4) alanine | (13) phenylalanine |
| (5) glycine | (14) glutamic acid |
| (6) serine | (15) aspartic acid |
| (7) valine | (16) cystine |
| (8) proline | (17) tyrosine |
| (9) isoleucine | |

Waveform:

| Waveform: | | | | |
| --- | --- | --- | --- | --- |
| E1: 200 | E2: 800 | E3: 200 | E4: 1000 | E5: −350 |
| Ta: 350 | Tb: 50 | Tc: 5 | Td: 1 | Td: 344 |
| Tf: 50 | Tg: 10 | Th: 100 | Ti: 90 | |

FIG. 13 contains a chromatogram obtained with the PS-PCD and pH reference with a slight change in the gradient elution conditions. The different conditions allowed separation of 20 amino acids. Again, the baseline is remarkably stable. LC-PCD of 20 amino acids
Electrodes: Au glass reference
Column: AS-8
Solutions: See Table III
Samples:

| (1) arginine | (11) isoleucine |
| (2) lysine | (12) leucine |
| (3) glutamine | (13) methionine |
| (4) asparagine | (14) histidine |
| (5) threonine | (15) phenylalanine |
| (6) alanine | (16) glutamic acid |
| (7) glycine | (17) aspartic acid |
| (8) serine | (18) cysteine |
| (9) valine | (19) cystine |
| (10) proline | (20) tyrosine |

Waveform:

| Waveform: | | | | |
| --- | --- | --- | --- | --- |
| E1: 200 | E2: 800 | E3: 200 | E4: 1000 | E5: −350 |
| Ta: 350 | Tb: 50 | Tc: 5 | Td: 1 | Te: 344 |
| Tf: 50 | Tg: 10 | Th: 100 | Ti: 90 | |

FIG. 14 shows the potential waveform for the PS-PCD separation process of FIGS. 12 and 13, and Table III below: shows a Table illustrating a solvent system for amino acid separation.

TABLE III

Solvent system for amino acid separation
with the Dionex AS-8 column:

| | |
|---|---|
| Solution #1 (regenerant): | 0.56 M NaOH/0.64 M boric acid |
| Solution #2: | 0.023 M NaOH/0.007 M $Na_2B_4O_7$ (0.005 M $Na_2B_4O_7$ substituted for LC-PAD and LC-PCD) |
| Solution #3: | 0.08 M NaOH/0.018 M $Na_2B_4O_7$/2% MeOH |
| Solution #4: | 0.4 M NaOAc/0.001 M NaOH/2% MeOH |

Flow Rate = 1.0 ml min$^{-1}$

Gradient Program

| Time (min) | Sol #1 % | Sol #2 % | Sol #3 % | Sol #4 % | inj val pos |
|---|---|---|---|---|---|
| 0.0 | — | 100 | — | — | inj |
| 4.0 | — | 100 | — | — | inj |
| 4.1 | 100 | — | — | — | −inj |
| 13.9 | 100 | — | — | — | inj |
| 14.0 | — | 100 | — | — | inj |
| 25.8 | — | 100 | — | — | load |
| 26.0 | — | 100 | — | — | inj |
| 36.0 | — | 100 | — | — | inj |
| 40.0 | — | — | 100 | — | inj |
| 46.0 | — | — | 100 | — | inj |
| 46.1 | — | — | 90 | 10 | inj |
| 56.0 | — | — | — | 100 | inj |

CONCLUSION

The design of the waveform for PS-PCD at a Au electrode can result in virtual elimination of baseline signals for oxide-catalyzed detection processes, and the technique is recommended in conjunction with a pH reference for liquid chromatographic separations which utilize pH-gradient elution over a limited pH range.

It should be clearly understood that the technique according to the present invention is for electrochemical detection of analyte in a liquid chromatographic environment.

The use of PS-PCD with a Au working electrode has been described, but this technique will work equally well with other electrode substrates, such as Pt, Ru, Rh, Pd, Pb, etc., for which an oxide layer can be formed and subsequently stripped at more cathodic potentials.

In general, this technique is applicable to the measurement of irreversible electrochemical processes superimposed or coincident with irreversible processes. The measurement of surface-oxide catalyzed reactions during the formation of surface oxide is a single example of the PS-PCD technique.

The PS-PCD technique is believed applicable to detection of compounds such as amino acides, carbohydrates and sulfur compounds. The PS-PCD technique is applicable to the detection of alcohols, polyalcohols, amines, alkanolamines, monosaccharides, disaccharides, oligosaccharides glycopeptides, glycoproteins, thiocarbonides, thiophosphates and inorganic sulfur.

As described herein, the PS-PCD method of the present invention is particularly applicable to detection of multiple chemical components in a liquid sample which have been separated by liquid chromatography, particularly high performance liquid chromatography (HPLC). The liquid sample is normally mixed with an eluent including an electrolyte as a developing reagent and passed through a chromatography column. The packing for the column typically would include gel or particulate forms of ion exchange or reverse phase packing. The technology is well developed. For example, see C. F. Simpson, *Techniques of Liquid Chromatography*, 1983, J. H. Knox, *High Performance Liquid Chromatography*, 1981, and K. Polkar et al., *Liquid Chromatography in Clinical Analysis*, 1981.

In addition, the PS-PCD method is useful as a method of detection in flow injection analysis (FIA). Such systems are described in Skeggs, Amer. J. Clin. Path., 28, 311–322 (1957) and in U.S. Pat. Nos. 4,013,413, 4,022,575, 4,177,677, 4,224,033, 4,227,973, 4,314,824, 4,315,754, 4,352,780, 4,399,102, 4,399,225, and 4,504,443. In such systems, these samples are supplied to the detector in a continuous liquid carrier flow rather than by being separated, e.g., in liquid chromatography. This technique is of limited application in comparison to the aforementioned liquid chromatographic system.

The list of reference is identified as follows:

REFERENCES

1. Hughes, S., Johnson, D. C., *Anal. Chim. Acta* 1981, 132, 11.
2. Hughes, S., Johnson, D. C., *Anal. Chim. Acta* 1983, 149, 1.
3. Edwards, P., Haak, K., *Amer. Lab.* 1983, April 78.
4. Rocklin, R. D., Pohl, C. A. *J. Lig. Chromatogr.* 1983, 6(9), 1577.
5. Neuburger, G. G., Johnson, D. C., *Anal. Chem.* 1987, 59, 150.
6. Neuburger, G. G. Johnson, D. C., *Anal. Chem.* 1987, 59, 203.
7. Polta, J. A., Johnson, D. C., *J. Lig. Chromatogr.*, 1983, 6, 1727.
8. Polta, J. A., Johnson, D. C., Merkel, K. E., *J. Chromatogr,* 1985, 324, 407.
9. Polta, T. Z., Luecke, G. R., Johnson, D. C., *J. Electroanal. Chem.* 1986, 209, 159.
10. Polta, T. Z., Luecke, G. R., Johnson, D. C., *J. Electroanal, Chem.* 1986, 209, 171.
11. Thomas, M. B., Sturrock, P. E., *J. Chromatogr* 1986, 357, 318.
12. Neuburger, G. G., Johnson, D. C., *Anal. Chim. Acta* 1987, 192, 205.
13. Polta, J. A., Yeo, I. H., Johnson, D. C., *Anal. Chem.* 1985, 1985, 57, 563.
14. Mead, D. A., M. S. Dissertation, Iowa State University, Ames, Iowa., 1988.

The scope of the present invention should therefore be construed only in conjunction with the accompanying claims.

What is claimed is:

1. A liquid chromatographic pulsed waveform coulometric detection method for detection of analyte where an electric potential sweep having a certain time period of duration which is applied to a working electrode in a flow-through cell, said method comprising the steps of
   electrochemically detecting analyte in a liquid chromatographic environment using a cyclic pulse waveform coulometric detection technique having a potential sweep or potential step function, including the step of applying current integration over the time period of said cyclic potential sweep.

2. The method as in claim 1 wherein said flow-through cell is a three electrode cell and wherein one of the electrodes is a pH reference electrode.

3. The method as in claim 2 wherein pH gradient elution is employed.

4. The method as in claim 1 further including the steps of generating multi-step potential waveforms having cyclic potential changes where the cyclic waveforms have a first initial potential value ($E_1$) for a first time period $t_d$ so that the electrode surfaces exist in an oxide-free state, advancing the potential value to a second, higher value ($E_{1'}$) for a time period $t_s$ so as to cause the formation of surface oxide with concurrent electrocatalytic oxidative reaction of soluble and/or absorbent analyte, returning the potential value to said first value $E_1$ for a holding time period $t_h$, during which all oxide formed during the potential change to $E_{1'}$ is cathodically stripped from said electrode surfaces.

5. A liquid chromatographic pulsed waveform coulometric method for use in an anodic cleaning and cathodic reactivation of electrode surfaces comprising the steps of generating multi-step potential waveforms having cyclic pulsed potential changes having a certain period of duration where the cyclic waveforms have a first initial potential value ($E_1$) for a first time period $t_d$ so that the electrode surfaces exist in an oxide-free state, advancing the potential value to a second, higher value ($E_{1'}$) for a time period $t_s$ so as to cause the formation of surface oxide with concurrent electrocatalytic oxidative reaction of soluble and/or adsorbent analyte, returning the potential value to said first value $E_1$ for a holding time period $t_n$, during which all oxide formed during the potential change to $E_{1'}$ is cathodically stripped from said electrode surfaces, said method including the step of applying current integration over the time period of said cyclic potential sweep.

6. The method as in claim 5 wherein the cyclic potential change is advanced according to a potential sweep function.

7. The step as in claim 5 or 6 wherein the cyclic potential change is advanced according to a potential step function.

8. The method as in claim 5 including the further step of advancing said potential value to a value $E_2$ higher than said first or second values for a period of time $t_2$ for oxidative cleaning of said electrode surface.

9. The method as in claim 5 or 8 including the further step of decreasing said potential value to a value $E_3$ lower than said first value for a time period $t_3$ for reactivation by cathodic dissolution of the surface oxide at $E_{1'}$ and/or $E_2$.

10. The method of liquid chromatography quantitative analysis of a plurality of multiple chemical components in a liquid sample solution, said method comprising flowing said solution through chromatographic separation means and separating said components upon elution therefrom, passing the effluent from said chromatographic means through a flow-through cell wherein an electric potential is applied to a working electrode, and electrochemically detecting the separated chemical components in the cell using a cyclic pulsed coulometric detection technique having a potential sweep or a potential step function of a certain time period of duration, said method including the steps of applying current integration over the time period of said cyclic potential sweep.

* * * * *